(12) United States Patent
Fukuda

(10) Patent No.: US 7,048,933 B2
(45) Date of Patent: May 23, 2006

(54) YEAST AND A FERMENTATION PRODUCT

(75) Inventor: Harui Fukuda, Fukushima (JP)

(73) Assignee: Koji Fukuda, Tokyo (JP)

( * ) Notice: Subject to any disclaimer, the term of this patent is extended or adjusted under 35 U.S.C. 154(b) by 0 days.

(21) Appl. No.: 10/389,430

(22) Filed: Mar. 14, 2003

(65) Prior Publication Data

US 2003/0175258 A1 Sep. 18, 2003

Related U.S. Application Data

(62) Division of application No. 10/169,874, filed as application No. PCT/JP01/05080 on Jun. 14, 2001, now abandoned.

(30) Foreign Application Priority Data

Jun. 14, 2000 (JP) ............................ P2000-184541

(51) Int. Cl.
*A61K 35/72* (2006.01)

(52) U.S. Cl. ............................... 424/195.16; 435/255.1

(58) Field of Classification Search ........... 424/195.16; 435/255.1
See application file for complete search history.

(56) References Cited

U.S. PATENT DOCUMENTS 5,618,707 A * 4/1997 Homann et al.

5,747,081 A 5/1998 Lee et al.

FOREIGN PATENT DOCUMENTS

| CN | 2001-497458 | 12/2000 |
|---|---|---|
| GB | 1527656 | 10/1978 |
| JP | 61282059 | 12/1986 |
| JP | 61289865 | 12/1986 |
| JP | 08322555 A * | 12/1996 |
| JP | 09107936 | 4/1997 |
| JP | 2001000141 | 1/2001 |

OTHER PUBLICATIONS

Leyva et al. (Enzyme and Microbial Technology (1999), vol. 24, pp. 270-275).*
Pelczar et al. (Microbiology: Concepts and Applications (1993); McGraw-Hill: USA, p. 282).*

* cited by examiner

*Primary Examiner*—Susan D. Coe
(74) *Attorney, Agent, or Firm*—Kilpatrick Stockton LLP

(57) ABSTRACT

Remedies for allergic diseases obtained by mixing shoots of plants belonging to the family Pinaceae with water and saccharides followed by spontaneous fermentation. As the plants belonging to the family Pinaceae, is preferable to use plants belonging to the genus *Pinus*. These remedies, which enable complete recovery in a short administration time without showing any side effects, are useful as remedies for allergic diseases, in particular, asthma and atopic dermatitis. Also, a yeast isolated from these remedies for allergic diseases is provided.

4 Claims, 5 Drawing Sheets

(A)

(B)

(A)

(B)

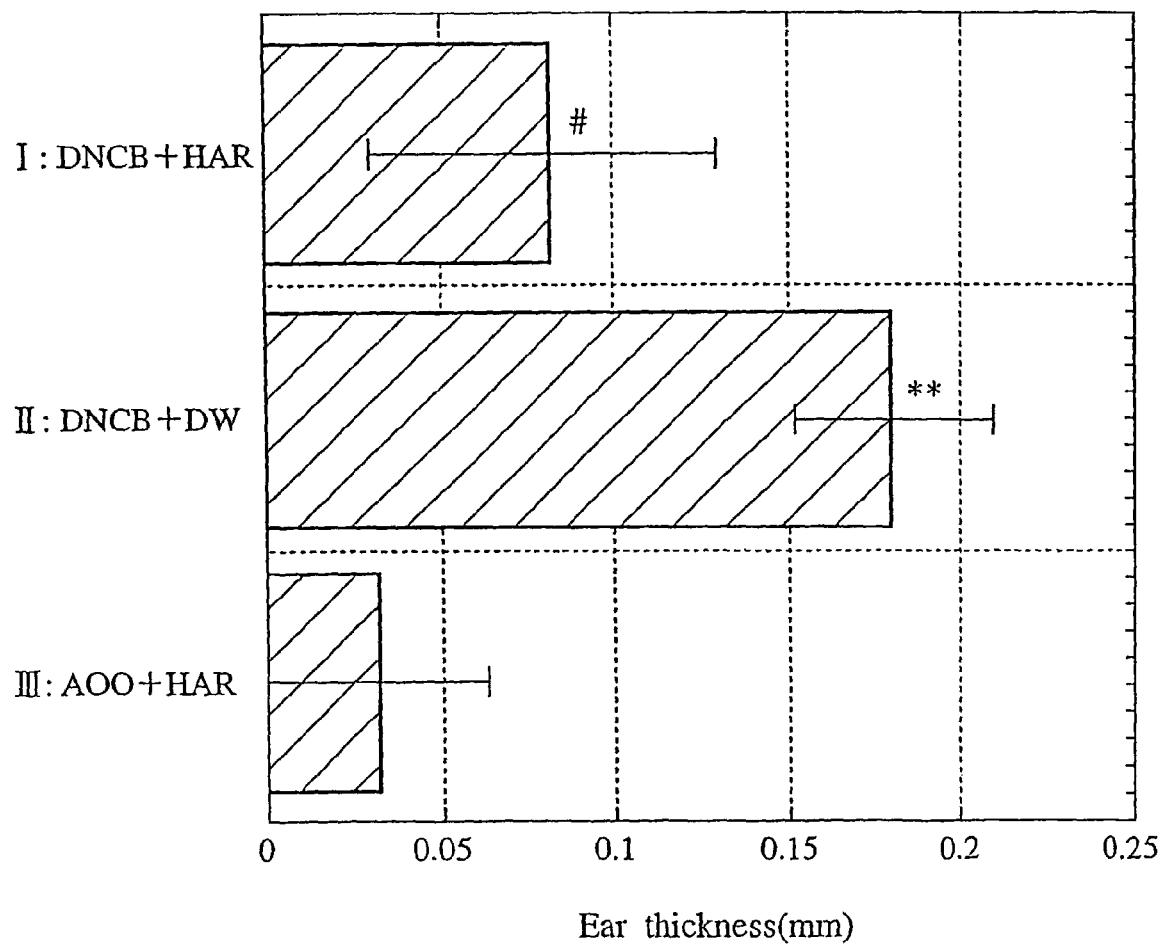

YEAST AND A FERMENTATION PRODUCT

CROSS-REFERENCE TO RALATED APPLICATION

This application is a divisional of U.S. application Ser. No. 10/169,874 filed on Jul. 3, 2002 now abandoned, which is a 371 of PCT/JP01/05080, filed Jun. 14, 2001.

The application has a right of priority based on Japanese Patent Application No. 2000-184541 filed in Japan on Jun. 14, 2000, all of the contents of the application are incorporated as parts of the specification of the instant application by reference.

TECHNICAL FIELD

The present invention relates to a remedy for allergic diseases, for example, asthma, atopic dermatitis, conjunctivitis, rhinitis and food allergy, and to a method of producing the same. Further, the present invention relates to yeast isolated from the above-mentioned remedy.

BACKGROUND ART

A human body has an immune system which is a defense mechanism which, when extraneous substances such as bacteria and viruses invade body, antagonizes them and protects body. Allergies are caused due to excess action of this immune system. Recently, increasing number of people are suffering from allergies possibly because of, though the details are not clear, air pollution, change of dietary life, physical or mental stress increase, environmental changes such as room pollution and the like due to change in resident circumstances, or change in human body constitution.

The allergic diseases include asthma, atopic dermatitis, allergic conjunctivitis, allergic rhinitis such as pollenosis, food allergy and the like.

The first remedy for these allergic diseases is to avoid the allergens, though the remedy is rather passive. When dusts or mites in a house are the allergens, the house must be cleaned to remove the allergens, and when a pollen is the allergen, in the season of the pollen floatation, going out should be held or a mask should be worn to prevent suction of the allergen, and in the case of a food allergy, the food causing the allergy should not be eaten. However, such a passive remedy is troublesome to the patient and significantly restricts the activities of the patient.

For remedy of asthma, the attack of asthma is stopped or is prevented by symptomatic treatments, and for these purposes, medicines such as sympathetic nervous drugs such as adrenalin, adrenal cortical steroid hormones, theophyllin drugs and the like are used. Though asthma is a disease sometimes leading the patient to death, there is still no remedy for complete recovery.

In infant period, atopic dermatitis causes distresses not only to the patient but also to the parents of the patient. Though the most of the patients are cured before maturity, there is a case where the dermatitis lasts to the adulthood. In such a case, adolescent men and women are distressed by thickening of the skin of face, breast, inside of elbow and knee and by severe itching. As the remedy for this, topical treatments are the major methods to treat the patient, and depending on the symptom, adrenal cortical hormones, antihistamine drugs and other anti-inflammatory agents are used. When itching is strong, systemic application of an antihistamine agent would be necessary.

However, these remedies are symptomatic therapies and do not completely remedy the allergies, and the side effects due to the use of the drugs are also caused.

When an allergen can be specified, there is a treatment called a sensitivity-reducing remedy in which the extract of the allergen is, first, injected to the patient hypodermically in very small amount, then, the amount is gradually increased to give a resistance against the allergen to the patient. However, in this remedy, the injection of the extract must be repeated on the patient periodically such as once to twice a week and the remedy requires a long period of time, additionally, an effect may not be sufficient enough in some patients, further, anaphylactic shock sometimes leading the patient to death may be caused in some incidents.

For remedy of asthma and atopic dermatitis, there are a lot of folk medicines, however, such medicines may worsen the symptom in some cases.

Given the current remedies for allergies as described above, the object of the present invention is to provide a remedy which can completely cure allergies by administrating the remedy in a short period of time without causing side effects, and a method of producing such a remedy.

DISCLOSURE OF THE INVENTION

The remedy for allergic diseases (allergies) of the present invention can be obtained by mixing shoots of plant belonging to the family Pinaceae with water and saccharides followed by spontaneous fermentation, and the remedy is effective for treating allergic diseases such as asthma, atopic dermatitis and the like. As the above-mentioned plant belonging to the family Pinaceae, plant belonging to the genus *Pinus* is preferable, and as the above-mentioned saccharides, sugar is preferable.

The remedy for allergic diseases of the present invention can be obtained by mixing shoots of pine leaves with water and sugar followed by spontaneous fermentation, and the remedy is effective for treating allergic diseases such as asthma, atopic dermatitis and the like.

Further, the present invention relates to a method of producing the above-mentioned remedy for allergic diseases, the method of producing the remedy for allergic diseases comprises (1) a step of dissolving saccharides in sterilized water to prepare a saccharides solution, and (2) a step of adding shoots of plant belonging to the family Pinaceae to said saccharides solution followed by spontaneous fermentation. As the above-mentioned plant belonging to the family Pinaceae, a plant belonging to the genus *Pinus* is preferable, and as the above-mentioned saccharides, sugar is preferable.

In another embodiment, the method of producing a remedy for allergic diseases of the present invention comprises (1) a step of dissolving sugar in sterilized water to prepare a solution containing dissolved sugar, and (2) a step of adding shoots of pine leaves to said solution containing dissolved sugar followed by spontaneous fermentation.

The above-mentioned spontaneous fermentation is preferably conducted under anaerobic conditions at 10 to 70° C., preferably 20 to 60° C. for about 3 to 9 months, preferably 4 to 8 months.

The more specific method of producing a remedy for allergic diseases comprises (1) a step of dissolving sugar in hot water to prepare a sugar aqueous solution then the solution being cooled to ambient temperature, and (2) a step of adding water-washed shoots of pine leaves to said sugar aqueous solution, placing the solution into a vessel and sealing the vessel followed by spontaneous fermentation, and the spontaneous fermentation is preferably conducted by placing the sealed vessel at a place receiving direct sunlight until early winter.

The present invention also contemplates a health food obtained by mixing shoots of plant belonging to the family Pinaceae with water and saccharides followed by spontaneous fermentation, and the health food is preferably obtained by mixing shoots of pine leaves with water and sugar followed by spontaneous fermentation.

Further, the present invention encompasses a fermentation products obtained by the spontaneous fermentation set forth above, namely, a novel yeast isolated from the remedy for allergies. The yeast has been deposited as HARUISAN A-3 with Independent Administrative Agency, National Institute of Advanced Industrial Science and Technology (AIST), International Patent Organism Depositary, Chuo No. 6, Higashi 1-1-1, Tsukuba City, Ibaraki Prefecture (old name: National Institute of Bioscience and Human-Technology National institute of Advanced Industrial Science and Technology, Higashi 1-1-3, Tsukuba City, Ibaraki Prefecture, name has been changed on Apr. 1, 2001) on Mar. 12, 2001, and specified by deposit No. FERM BP-7499. A series of yeasts having the microbiological properties equivalent to the deposited yeast are also included in the present invention. Further, in the present invention, a fermentation product obtained by the fermentation using the above-mentioned yeast is included, and as the fermentation product, pharmaceutical preparations such as allergic curative medicines, health foods, health drinks, and raw materials of cosmetics, and the like are exemplified. Here, the health food and health drink indicate foods and drinks such as supplements and the like used for the purpose of improving body constitution and maintaining health.

BRIEF DESCRIPTION OF DRAWINGS

In FIG. 4, the contraction ratio of an extracted trachea from a guinea pig sensitized with ovalbumin (OVA) is plotted against the dose of OVA when a remedy for allergies of the present invention is applied to the organ bath. In the figure, "A" represents a result in group I, and "B" represents a result in group II. ○ represents control (injection water), and ● represent a result in the case of addition of 0.02% of a remedy for allergies of the present invention. * represents $p<0.05$, significant as compared with the control.

FIG. 5 is a graph showing the drug effect of a remedy for allergies of the present invention, and shows the result of an ear swelling test (ear edema thickness measuring test). In the figure, 1-chloro-2,4-dinitrobenzene (DNCB) and a remedy for allergies of the present invention (abbreviated as HAR) are administered in group I, DNCB and injection water (distilled water: DW) are administered in group II, and acetone-olive oil mixture (4:1) and a remedy for allergies of the present invention (abbreviated as HAR) are administered in group III. * * represents $p<0.01$, significant for group III, and # represents $p<0.05$, significant for group II.

THE BEST MODE FOR CARRYING OUT THE INVENTION

Figure 1:
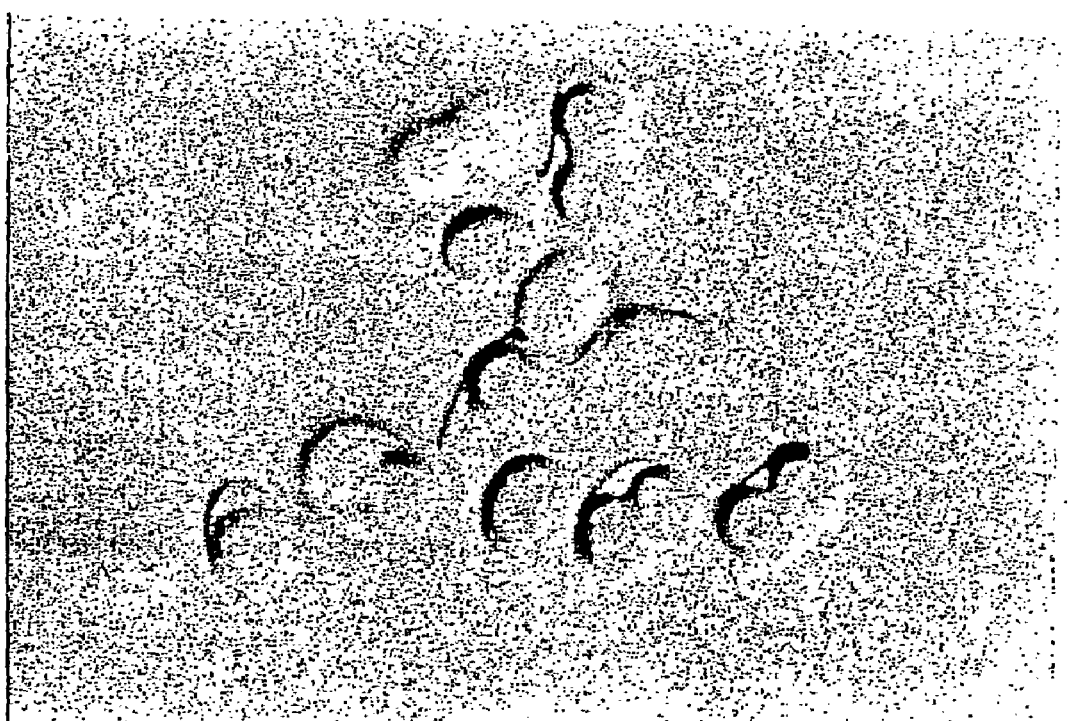
FIG. 1 is a microscopic photograph (differential interference, X 2400) showing an example of the ascospore of isolated yeast isolated from the remedy for allergies (fermentation product) of the present invention. As the medium, malt extract agar medium was used.

The remedy for allergies of the present invention is obtained by mixing shoots of plant belonging to the family Pinaceae with water and saccharides followed by spontaneous fermentation.

As the plant belonging to the family Pinaceae that can be used in the present invention, exemplified are *Abies firma* Sieb. & Zucc., *Abies homolepis* Sieb. & Zucc., *Abies mariesii* M. T. Mast., *Abies sachalinensis* (Friedr, Schmidt) M. T. Mast. var *marie*, *Abies sachalinensis* (Friedr, Schmidt) M. T. Mast., *Abies veitchii* Lindl., *Cedrus deodara* (Roxb. ex D. Don) G. Don, *Larix gmelini* (Rupr.) Kuzeneva, *Larix Kaempferi* (Lamb.) Carriere, *Picea abies* (L.) Karst., *Picea glehnii* (Friedr. Schmidt) M. T. Masters, *Picea jezoensis* (Sieb. & Zucc.) Carriere var. *hondoensis*, *Picea jezoensis* (Sieb. & Zucc.) Carriere, *Picea koyamae* Shirasawa, *Picea polita* (Sieb. & Zucc.) Carriere, *Pinus* x densi-thunbergii Uyeki, *Pinus densiflora* Sieb. & Zucc., *Pinus densiflora* Sieb. & Zucc. cv. Umbraculifera, *Pinus koraiensis* Sieb. & Zucc., *Pinus palustris* Mill., *Pinus parviflora* Sieb. & Zucc. var. *parviflora*, *Pinus parviflora* Sieb. & Zucc. var. *pentaphylla* (Mayr) Henry, *Pinus pumila* (Pall.) Regel, *Pinus rigida* Mill., *Pinus strobus* L., *Pinus sylvestris* L., *Pinus teada* L., *Pinus thunbergii* Parl., *Pseudotsuga japonica* (Shiras.) Beissn., *Tsuga diversifolia* (Maxim.) M. T. Mast., *Tsuga Sieboldii* Carriere and the like. Of them, *Pinus* x densi-thunbergii Uyeki, *Pinus densiflora* Sieb. & Zucc., *Pinus densiflora* Sieb. & Zucc. cv. Umbraculifera, *Pinus koraiensis* Sieb. & Zucc., *Pinus palustris* Mill., *Pinus parviflora* Sieb. & Zucc. var. *parviflora*, *Pinus parviflora* Sieb. & Zucc. var. *pentaphylla* (Mayr) Henry, *Pinus pumila* (Pall.) Regel, *Pinus rigida* Mill., *Pinus strobus* L., *Pinus sylvestris* L., *Pinus teada* L. and *Pinus thunbergii* Parl. which are plants belonging to the genus *Pinus* are preferable, and particularly, *Pinus densiflora* Sieb. & Zucc., *Pinus densiflora* Sieb. & Zucc. cv. Umbraculifera, *Pinus koraiensis* Sieb. & Zucc., *Pinus palustris* Mill., *Pinus pumila* (Pall.) Regel, *Pinus thunbergii* Parl. and the like are generally grown pine trees, and also preferable from the standpoint of easy availability.

As the saccharides can be used in the present invention, sucrose, invert sugar, maltose and the like are exemplified. Of them, sucrose is preferable from the standpoint of easy availability, and as the sucrose used, any sugar such as white sugar, black sugar, yellow soft sugar, beet sugar, millet sugar and the like can be used, and white sugar is preferable.

As the water can be used, previously sterilized water is preferably used to prevent proliferation of saprophytic bacteria, and as the sterilization method, any known methods generally employed to sterilize water can be used, for example, water can be sterilized by boiling and the like.

The remedy for allergies of the present invention can be obtained by dissolving saccharides in the above-mentioned sterilized water to prepare a saccharides aqueous solution, adding to the saccharides aqueous solution a shoots of plant belonging to the family Pinaceae, and subjecting the mixture to spontaneous fermentation. The shoots of plant belonging to the family Pinaceae to be added to said aqueous solution may be a shoots collected from any kind of plants belonging to the family Pinaceae, and particularly, a shoots collected from a plant belonging to the genus *Pinus* is preferable. The preferable season for collecting the shoots is the season after completion of blooming of the plant, and the shoots collected in this season has the highest effectiveness as a remedy for allergies and therefore is preferable. In the case of pine tree, though it depends on climate of the land, reddish female flower blooms at the peak of a branch and yellow male flower blooms around the new branch generally around early April to late June, therefore, the shoots at the peak of the branch are preferably collected and used when blooming of these flowers is completed.

For preparing the starting solution used in the fermentation, about 0.5 kg of saccharide is dissolved in 1 liter of water. Then, to the resulting solution, about 25 shoots of plant belonging to the family Pinaceae are added. In this case, the saccharide is not required to be completely dissolved and there is no problem if the saccharide presents remaining undissolved in the solution. The starting solution to be fermented may advantageously contain shoots of plants belonging to the family Pinaceae such as shoots of pine leaves in the ratio set forth in the above, and there is no problem if it contains leaves and flowers other than the shoots.

The spontaneous fermentation can be conducted under anaerobic conditions and the fermentation is effected by allowing the starting solution to stand still at 10 to 70° C., preferably 20 to 60° C. for 3 to 9 months, preferably 4 to 8 months. As the anaerobic condition, for example, the starting solution is filled into a light-shielded vessel and the like and the vessel is sealed air tightly. The fermentation is realized by placing this sealed vessel at a place receiving direct sunlight until around early winter. After the period of spontaneous fermentation is completed, the vessel is opened, and the solid materials such as shoots of plant belonging to the family Pinaceae are removed to obtain a remedy for allergies of the present invention. The above-mentioned early winter is determined in consideration of the shoots collecting period, namely, charging period, and if the blooming period is from early April to early May and if the shoots collection period after completion of blooming is from middle May to early June in the producing area, the period of fermentation completion shall be early winter (middle November), however, this is only one example, and this period can optionally be changed.

The remedy for allergies of the present invention is effective for allergic diseases, particularly, asthma and atopic dermatitis, and in view of the mode of the action, the remedy is believed to be effective for improvement and treatment of, in addition to the above-mentioned diseases, type I allergic diseases such as anaphylactic shock by drugs, allergic rhinitis, acute urticaria, pollenosis, food allergy and the like, type II allergic diseases such as autoimmune hemolytic anemia, haemolysis and thrombocytopenia due to drug allergy, type II allergic diseases such as serum diseases, SEL, acute nephritis, polyarteritis and the like, type IV allergic diseases such as contact dermatitis, allergic encephalitis and the like.

The remedy for allergies of the present invention uses a fermentation product per se obtained by the spontaneous fermentation, however, a sweetener and flavoring agent may be added to the product to improve the acceptance of the product in drinking, or various additives such as a preservative and the like may be added for storing the product for a long period of time or for other purposes.

For the application of the remedy for allergies of the present invention, in the case of adult, in general, about 30 to 50 ml of the remedy is administered twice or three times a day. In the case of child, half dosage of that in the adult administration may be used. Since the remedy for allergies of the present invention has no toxicity and no mutagenicity and therefore is safe, there is no problem if an amount over the above-mentioned dosage is used.

The fermentation product of the present invention obtained by the spontaneous fermentation can be used not only as a remedy for allergies but also as health food or health drink. The health food or health drink are not used mainly for remedy, but used to improve body constitution and maintain healthy condition. In this case, it is preferable, in view of inclination of consumers, to add the above-mentioned sweetener, flavoring agents or the like to make the product acceptable to drink or eat and to make the product compatible with the inclination.

Further, the present invention includes yeast isolated from the above-mentioned fermentation product. This yeast is isolated as described below.

A fermentation product which is the remedy for allergies of the present invention was used as the specimen. GPLP agar plate culture method was used to culture the microorganisms on the plate, and the colonies dominantly grown on the culture plate were picked up to obtain the isolate yeast. On the isolated yeast, the morphological and physiological observations were performed, and the yeast was identified by consulting literatures Kurtzman, C. P. et al. (eds.) "The Yeasts, A Taxonomic Study" 4-th edition (1998), Elsevier Science; B. V.; Barnett, J. A. et al. (eds.), "Yeasts: Characteristics and Identification" 3-rd edition (2000), Cambridge University Press these literatures are incorporated as part of the specification of the instant application by reference). The total number of yeast in the fermentation product was $1.4 \times 10^5$/g. The results form the morphological and physiological observations on the isolated yeast are shown in Table 1 and an example of ascospore of the isolated yeas is shown in FIG. 1.

TABLE 1

Properties of the Isolated Yeast

| Item Observed | Result |
|---|---|
| Form of nursing cell | Oval to ellipse |
| Proliferation form | Multiple budding |
| Liquid culture | Sedimentation observed, no film formation observed (25° C., 3 days) |
| Pseudohypha | Formed (25° C., 3 days) |
| Ascospore | Mating observed between individual nursing cells, 1 to 4 ascospores in the form of ellipse formed, ascus not divided (see FIG. 1) |
| Utility of nitrogen source: | |
| Nitrate | − |
| Ethylamine | + |
| Growth in vitamin-deficient medium | − |
| Growth in the presence of NaCl: | |
| 10% | + |
| 12.5% | + |
| 15% | Weak |

TABLE 1-continued

Properties of the Isolated Yeast

| Item Observed | Result |
|---|---|
| 16% | − |
| Growth in the presence of cycloheximide: | |
| 0.1% | − |
| 0.01% | − |
| Growth in the presence of 1% acetic acid | + |
| Growth at 37° C. | − |
| Degradation of urea | − |
| Coloration of DBB | − |
| Fermentation property: | |
| Glucose | + |
| Galactose | − |
| Sucrose | − |
| Maltose | − |
| Lactose | − |
| Raffinose | − |
| Trehalose | − |
| Utilization of carbon source: | |
| Glucose | + |
| Galactose | − |
| Sucrose | − |
| Maltose | − |
| Cellobiose | − |
| Trehalose | − |
| Lactose | − |
| Melibiose | − |
| Raffinose | − |
| Melezitose | − |
| Starch | − |
| D-xylose | − |
| L-arabinose | − |
| D-ribose | − |
| L-rhamnose | − |
| D-glucosamine | − |
| N-acetyl-D-glucosamine | − |
| Ethanol | + |
| Glycerol | + |
| Erythritol | − |
| Ribitol | + |
| D-mannitol | + |
| Citrate | − |
| Inositol | − |

According to the above results, the isolated yeast is identified as *Zygosaccharomyces bisporus* from the morphological and physiological properties. The *Zygosaccharomyces bisporus* belongs to ascomycetous yeast, mates between the individual cells and forms 1 to 4 ascospores of sphere to ellipse form. Further, *Zygosaccharomyces bisporus* is osmosis resistant yeast and isolated from fermentation foods, soft drinks and the like.

Moreover, a DNA homology test was conducted between the isolated yeast and the type strain to give the following results. Namely, *Zygosaccharomyces bisporus* IFO 1131 and *Zygosaccharomyces bailii* IFO 1098 were used as the type strains according to Takayuki Ezaki et al., Japanese Journal of Bacteriology, vol. 45, p. 851 (1990) and Masaaki Takahashi et al., Tokyo University of Agriculture Isotope Center Study Report, No. 7, p. 69 (1993), both of which literatures are incorporated herein by reference. The DNA homology test between them and the isolated yeast was carried out by a photo biotin labeling method using a microplate, in a DNA—DNA hybridization test. The preparation of DNA was conducted according to Jahnke, K. -D. et al., Trans. Br. Mycol. Soc., Vol. 87, pp. 175–191 (1986)(this literature is incorporated as parts of the specification of the instant application by reference). The results are shown in Table 2.

TABLE 2

Results of DNA-DNA Hybridization Homology Test between Isolated Yeast and Type Strain

| Type strain | Homology (%) |
|---|---|
| *Zygosaccharomyces bisporus* IFO 1131 | 72 |
| *Zygosaccharomyces bailii* IFO 1098 | 98 |

According to the results of the homology test with the above-mentioned type strains, though the yeast of the present invention is identified as *Zygosaccharomyces bisporus* from the morphological and physiological properties, DNA sequence itself is close to *Zygosaccharomyces bailii* rather than *Zygosaccharomyces bisporus*. Accordingly, it is recognized that the yeast of the present invention is a novel strain differing from both type strains. The applicant named this novel yeast as "HARUISAN A-3" which is deduced to belong to *Zygosaccharomyces* genus. Presently, it is not clear whether this novel yeast "HARUISAN A-3" is just a novel strain or is a novel species or genus. However, the applicant deposited the novel yeast isolated and named "HARUISAN A-3" with Independent Administrative Agency, National Institute of Advanced Industrial Science and Technology (AIST), International Patent Organism Depositary, Chuo No. 6, Higashi 1-1-1, Tsukuba City, Ibaraki Prefecture, Japan (old name: National Institute of Bioscience and Human-Technology National institute of Advanced Industrial Science and Technology, Higashi 1-1-3, Tsukuba City, Ibaraki Prefecture, Japan, in accordance with the Budapest Treaty on the International Recognition of the Deposit of Microorganisms for the Purposes of Patent Procedure, on Mar. 12, 2001, under a deposit number of FERM BP-7499. The above-mentioned Depositary was turned into an independent administration corporation on Apr. 1, 2001, and altered as Independent Administrative Agency, National Institute of Advanced Industrial Science and Technology (AIST). Thus, the name was changed on Apr. 1, 2001.

The isolated novel yeast of the present invention is believed to significantly contribute to effectiveness of the remedy for allergies together with shoots of plants belonging to the family Pinaceae, and therefore is extremely useful yeast.

Next, the remedy for allergies of the present invention is described in detail by examples, but the scope of the invention is not limited to the following examples.

The remedy for allergies of the present invention can be produced, for example, by the following method.

Shoots of pine leaves of *Pinus thunbergii* Parl., *Pinus densiflora* Sieb. & Zucc. and *Larix kaempferi* (Lamb.) Carriere were collected when pine blooming was completed (in Fukushima prefecture in Japan, around middle May to early June), and the collected shoots of pine leaves were washed thoroughly with water. White sugar was added and dissolved into hot water, and cooled to around room temperature, and the resulting sugar water and water-washed shoots of pine leaves were placed in a vessel, for example, a plastic vessel, the vessel is sealed, and the vessel is placed at a place receiving direct sunlight until early winter (around middle November, in Fukushima pref.) to cause spontaneous fermentation for the production. The vessel was opened around early winter, and the pine leaves were removed to obtain the remedy for allergies of the present invention.

For the sugar water used, about 1 kg of white sugar was used per about 2 liters of water, and 50 pine leaves were used per about 2 liters of water.

As described above, the production was conducted using 1 kg of white sugar and about 50 pine leaf shoots were used per about 2 liter of water, which resulted in about 1.2 liter (about 60% of the charged sugar water) of a remedy for allergies in the form of liquid having white turbidity. The components of the remedy and the content were analyzed, and the results are shown in Table 3.

TABLE 3

Analyzed Values of Components of Remedy for Allergies

| Component | Content | Analysis method used |
|---|---|---|
| Moisture | 98.0% | Guidelines for food hygiene inspection "Shyokuhin Eisei Kensa Shishin", normal pressure heating method |
| Protein | 0.0% | Guidelines for food hygiene inspection "Shyokuhin Eisei Kensa Shishin", Nitrogen quantification conversion method |
| Lipid | 0.4% | Guidelines for food hygiene inspection "Shyokuhin Eisei Kensa Shishin", ether extraction method (Soxhlet method) |
| Ash | 0.1% | Guidelines for food hygiene inspection "Shyokuhin Eisei Kensa Shishin", direct ashing method |
| Saccharides | 1.5% | Guidelines for food hygiene inspection "Shyokuhin Eisei Kensa Shishin", Calculated. |
| Crude fiber | 0.0% | Guidelines for food hygiene inspection "Shyokuhin Eisei Kensa Shishin", modified Henneberg Stoman method |
| Dietary fiber | 2.4% | Guidelines for food hygiene inspection "Shyokuhin Eisei Kensa Shishin", Prosky method |
| Na | 5.1 mg/100 g | Guidelines for food hygiene inspection "Shyokuhin Eisei Kensa Shishin" |
| P | Less than 0.50 mg/100 g*[1] | Guidelines for food hygiene inspection "Shyokuhin Eisei Kensa Shishin" |
| Fe | 0.11 mg/100 g | Guidelines for food hygiene inspection "Shyokuhin Eisei Kensa Shishin" |
| Ca | 1.66 mg/100 g | Guidelines for food hygiene inspection "Shyokuhin Eisei Kensa Shishin" |
| K | 18.3 mg/100 g | Guidelines for food hygiene inspection "Shyokuhin Eisei Kensa Shishin" |
| General bacteria | 2700 c.f.u./g | Guidelines for food hygiene inspection "Shyokuhin Eisei Kensa Shishin" |
| Escherichia coli | Negative | Guidelines for food hygiene inspection "Shyokuhin Eisei Kensa Shishin" |
| Thiamine | Less than 0.01 mg/100 g*[1] | HPLC method |
| Riboflavin | Less than 0.01 mg/100 g*[1] | HPLC method |
| Ergosterol | 0.07 mg/100 g | HPLC method |
| Niacin | 0.04 mg/100 g | Bioassay using microorganism*[2] |
| β-glucan | 0.03 mg/100 g | Enzyme method |

*[1]less than detection limit
*[2]Strain used: *Lactobacillus plantarum* ACTT 8014

This analysis was conducted only on the above-mentioned inspection items mainly regarding general food, and there is a possibility that the remedy for allergies of the present invention contains other components than the above components. Therefore, it could not be specified which component was particularly important as a remedy for allergies, however, the remedy was effective in treating allergies.

Next, with respect to a plurality of remedies for allergies of the present invention produced as described above, number of fungi, number of yeast and number of general bacteria (viable bacteria) contained in the remedy were counted. The number of fungi and the number of yeast were measured by using GPLP agar plate culture method, and the number of general bacteria (viable bacteria) was measured by using the anti-fungus agent-added SCDLP agar plate culture method in two ways, namely, pH of the medium was controlled to 3.5 using tartaric acid; pH of the medium was not controlled. The results are shown in Table 4.

TABLE 4

Number of Microorganisms Contained in the Remedy for Allergies

| Microorganism | Number/0.1 g | Fermentation product 1 | Fermentation product 2 | Fermentation product 3 | Fermentation product 4 |
|---|---|---|---|---|---|
| Number of fungi | Number/0.1 g | Negative | Negative | Negative | Negative |
| Number of yeast | Number/g | $1.3 \times 10^2$ | $3.3 \times 10^5$ | $1.6 \times 10^5$ | $3.3 \times 10^4$ |
| Number of general bacteria | Number/g | 100 or less | 100 or less | — | — |
| Number of general bacteria, pH controlled | Number/g | 100 or less | 100 or less | 100 or less | 100 or less |

According to the above results, the growth of fungus was not recognized in the remedy for allergies of the present invention, and the number of general bacteria (viable bacteria number) was also extremely small. Further, it can be understood that yeast was present in the order of $10^2$ to $10^5$/g in the fermentation product, though the yeast concentration was slightly irregular depending on the lot of the fermentation product. The yeast existed in the above fermentation products corresponded to the deposited novel yeast.

Next, the oral toxicity of the remedy for allergies of the present invention was examined. The stock solution of the remedy for allergies of the present invention and that obtained by adding honey (10 wt %) to the stock solution were used as the specimens. Two test groups each consisting of 5 male and 5 female SD [Crj: CD(SD)IGS] rats were administered the stock solution or the honey added stock solution at a rate of 2000 mg/kg and the control group was administered the injection water (dose: 0 mg/kg) alone. The specimens and the injection water were forcibly administered to the rats orally by using a disposable syringe (volume: 1 mL) equipped with a per os stomach conductor. The toxic symptom and approximate lethal dose were investigated over the period of 15 days after the administration (including administration day).

Throughout the test period, no death incident was observed in either of male and female rats in the group orally administered the remedy for allergies of the present invention and in the group administered the specimen prepared by adding honey to the remedy at the rate of 2000 mg/kg, including the control group. Moreover, no change ascribed to administration of the specimens was recognized in general condition, body weight and autopsy of the rats. From the above results, it was concluded that the approximate lethal dose of the remedy for allergies of the present invention under the conditions of this test was 2000 mg/kg or more for both male and female.

Next, the mutagenicity of the remedy for allergies of the present invention was investigated. Regarding the mutagenicity of the remedy for allergies of the present invention, the remedy for allergies was applied to the histidine-dependent *Salmonella typhimurium*, TA98, TA100, TA1535 and TA1537 strains, and tryptophan-dependent *Escherichia coli*, WP2uvrA strain according to the revised plate method of Ames et al. (Maron, D. M. et al., "Revised methods for the Salmonella mutagenicity test", Mutation Res., Vol. 113, pp. 173 to 215 (1983), this literature is incorporated as parts of the specification of the instant application by reference), and the mutagenicity was investigated under the presence of the metabolism activation or the absence of the metabolism activation.

Figure 2:
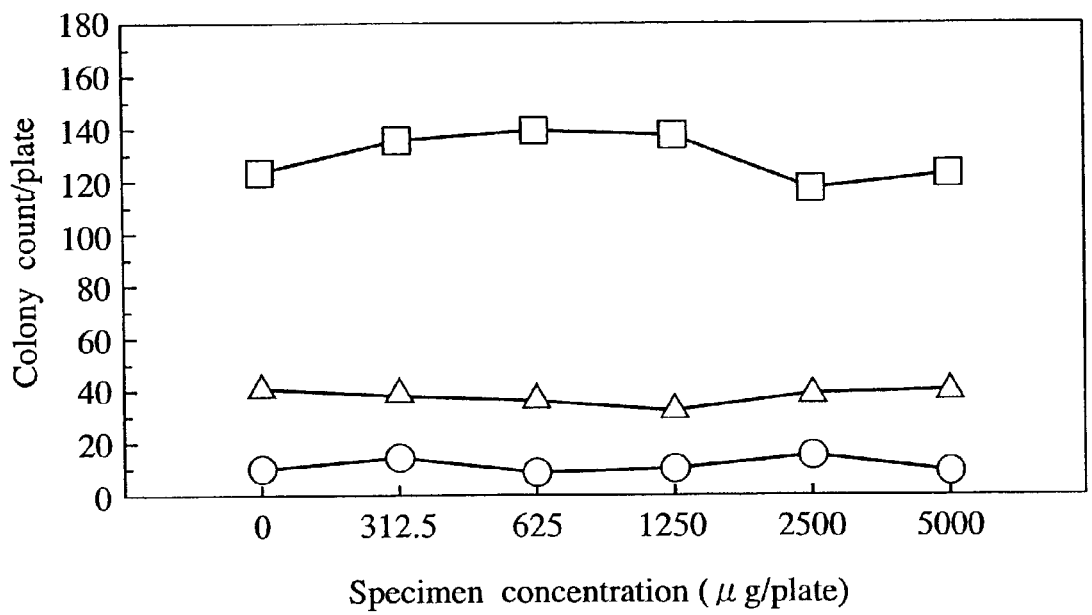
FIG. 2 shows the results of the mutagenicity screening tests made on a remedy for allergies of the present invention, where base pair-substituted type strains are used (TA100: □, TA1535: ○, WP2uvrA: Δ). In the figure, "A" represents a result in the case of utilizing no metabolism activation (−S9), and "B" represents a result in the case of utilizing metabolism activation (+S9), respectively.
Figure 2:
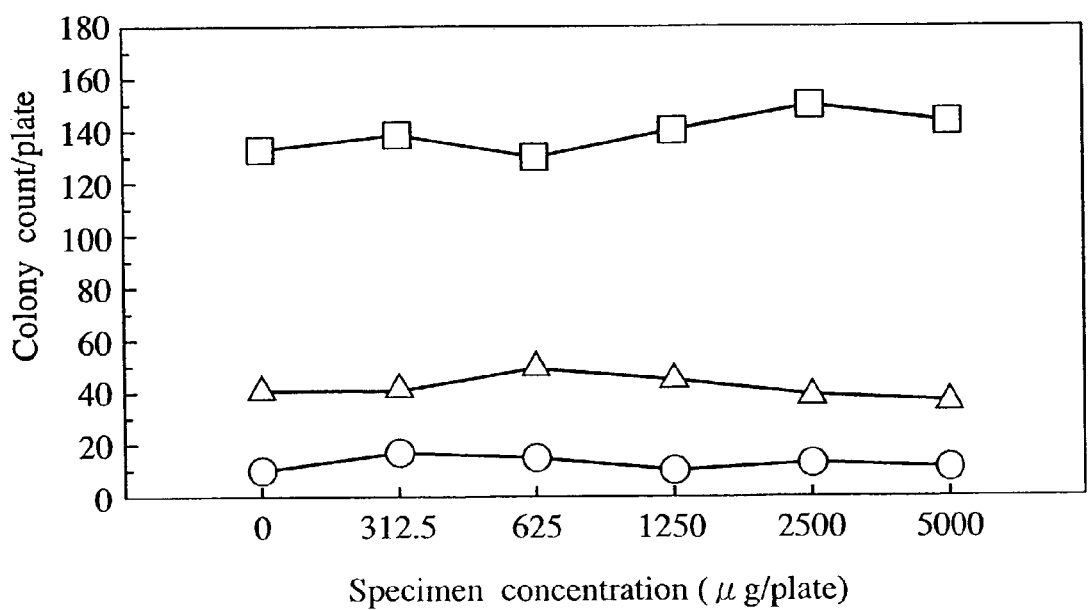
Figure 3:
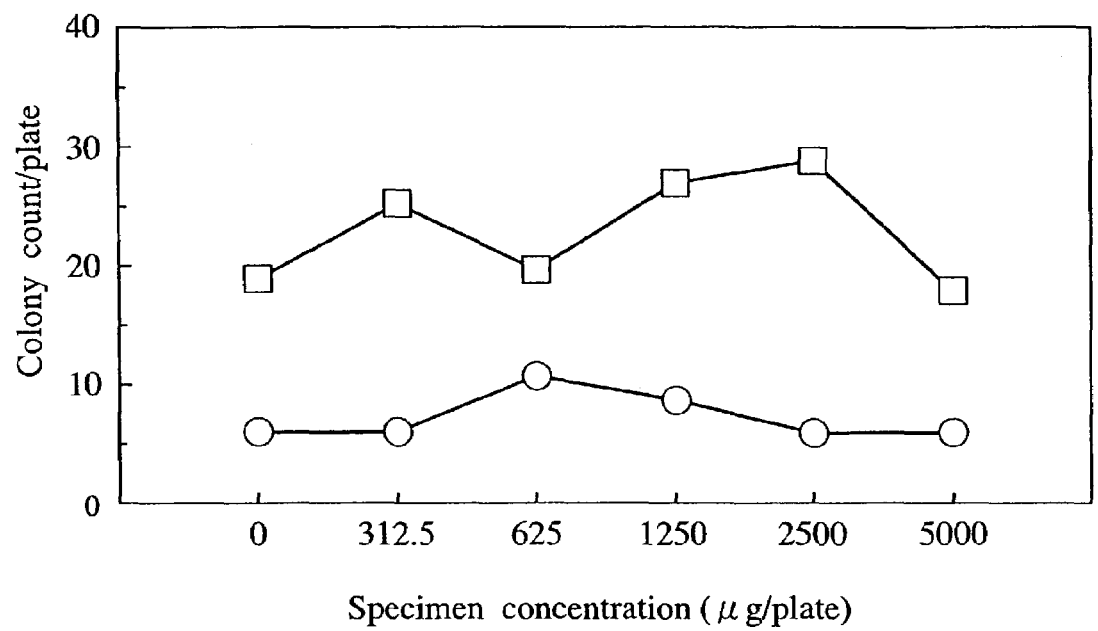
FIG. 3 is a graph showing the results of the mutagenicity screening test of on a remedy for allergies of the present invention, and shows the results obtained by using a frame shift type strain (TA98: □, TA1537: ○). In the figure, "A" represents a result in the case of utilizing no metabolism activation (−S9), and "B" represents a result in the case of utilizing metabolism activation (+S9), respectively.
Figure 3:
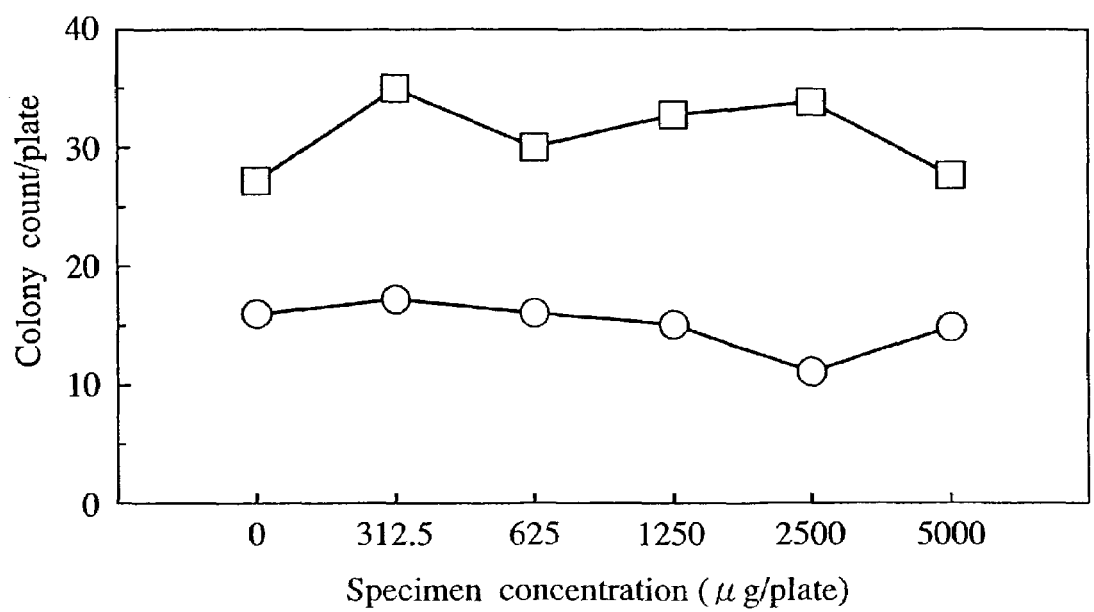

Those tests were conducted at a dose of 312.5, 625, 1250, 2500 and 5000 μg/plate of the remedy of the present invention. As the results, the number of the reverse mutation colonies of each test strain in the specimen group showed no increase in the dose-dependent manner and no increase over 2-fold or more was observed as compared to the negative control, irrespective of presence or absence of metabolism activation system. Further, no growth inhibition and no precipitation of the specimen were recognized. The results are shown in FIGS. 2 and 3. FIG. 2 shows the result in the base pair-substituted type strain (TA100: □, TA1535: ○, WP2uvrA: Δ). In the figure, "A" represents the result in the absence of the metabolism activation, and "B" represents the result in the presence of the metabolism activation to which S9 mix was added. FIG. 3 shows the results in the frame shift type strain (TA98: □, TA1537: ○). In the figure, "A" represents the result in the absence of the metabolism activation, and "B" represents the result in the presence of the metabolism activation to which S9 mix was added. As the negative control substance, distilled injection water that was used as the solvent to prepare the specimen was administered. As the positive control substance, compounds: 2-(2-Furyl)-3-(5-nitro-2-furyl)acrylamide (AF-2), 2-Aminoanthracene (2-AA), Sodium azide (SA) and 9-Aminoacridine (9-AA), were used. AF-2, 9AA and 2-AA were dissolved in DMSO and SA was dissolved in distilled injection water, respectively, and used depending on the strain and on the presence or absence of the metabolism activation.

From the above results, it was judged that the mutagenicity of the remedy for allergies of the present invention under the conditions of this test was negative.

Next, the pharmacological action of the remedy for allergies of the present invention was investigated. The action of the remedy of the present invention on the smooth muscle contraction using a guinea pig extracted trachea was examined to estimate the anti-asthma action which is one of the anti-allergy actions. Further, an ear swelling test was conducted to demonstrate the efficacy of the remedy of the present invention in improving atopic dermatitis which is one of allergic contact dermatitis.

1. Smooth Muscle Contraction Test using Guinea Pig Extracted Trachea

22 Hartley male guinea pigs (clean) of 5 weeks old were purchased. The animals were previously bred and quarantined for 1 week and 20 animals revealing no abnormality during the previous bred period were selected and used in the main test. The smooth muscle contraction test was conducted as described below.

The remedy for allergies of the present invention was diluted with injection water to give a solution of a specific concentration. Ovalbumin (OVA) used as an allergy inducing substance was dissolved in physiological saline. In sensitization administration for guinea pig, OVA and Freund's complete adjuvant (FCA) were mixed at equivalent amount, to give an administration specimen.

1-1) Sensitization Method

The animals were divided into 4 groups as follows.

TABLE 5

Constitution of Each Group

| Group | Administration substance and dose (administration volume) | | Number of animals |
|---|---|---|---|
| | Sensitization (subcutaneously, 0.2 mL) | Specimen (orally, 2 mL) | |
| I | 0.5% OVA is mixed with the same volume of FCA | 4% fermentation product of the present invention | 5 |
| II | 0.5% OVA is mixed with the same volume of FCA | Injection water | 5 |
| III | Physiological saline | 4% fermentation product of the present invention | 5 |
| IV | No-treatment | No-treatment | 5 |

OVA or physiological saline for sensitization was administered subcutaneously twice a week for two weeks, 4 time in total. The specimen, i.e., the remedy for allergies (fermentation product) of the present invention or injection water was orally administered to the animals for 3 days, i.e., preceding 3 days before the day of tracheal extraction (isolation).

Trachea was extracted from one animal from each group over 5 days from 11 day after the final sensitization administration, and a smooth muscle contraction test was conducted. Further, in extracting trachea, abdominal section was carried out and the blood was collected from inferior vena cava to obtain the serum, and the serum anti-OVA IgG antibody value was measured to confirm the establishment of sensitization, and an influence by oral administration of the above-mentioned remedy for allergies of the present invention was also investigated.

1-2) Smooth Muscle Contraction Test using Extracted Trachea

To animals having body weights of 520.7 to 681.5 were intraperitoneally admnistered 30 mg/kg of sodium pentobarbital for anesthetization. Breast was sectioned and trachea was extracted, and the chain preparation of the trachea was made in Krebs-Henseleit solution. Variation in tension of the trachea sample at a load of 0.5 g was isotonically measured by a variation transducer (45374, NEC San-ei Instruments, Ltd.) and recorded by a recorder (RECTI-HORIZ-8K, NEC San-ei Instruments) in 37° C. Krebs-Henseleit solution aerated with 95% $O_2$-5% $CO_2$ mixed gas. First, contraction was induced by $10^{-4}$ M acetylcholine, and this contraction was regarded as 100%. Influences of oral administration of the remedy for allergies of the present invention on induced contractions by 0.1 to 1000 ng/mL OVA, $10^{-8}$ to $10^{-3}$ M histamine and $10^{-5}$ to $10^{-4}$ M acetylcholine were observed. In addition, the remedy for allergies of the present invention was directly applied to the organ bath (final concentration: 0.02%, incubation for 10 minutes), and the influence by the application was investigated.

1-3) Measurement of Anti-OVA IgG Antibody Value

A micro titre plate (NUNC) on which OVA had been fixed was blocked with Block Ace (manufactured by Dainippon Pharmaceutical Co., Ltd.) and the blocked plate was used for the measurement.

The serum was diluted with BPS-Tween 10, $10^2$, $10^3$ and $10^4$-fold, and 100 μL of each diluted serum was added to the well, respectively (N=2).

After reaction at room temperature for 2 hours, then, the wells were washed with BPS-Tween. Then, an alkali phosphatase-labelled anti-guinea pig IgG diluted 1000-fold with Block Ace solution (10-fold diluted, including 0.05% $NaN_3$) was added to the each well at the amount of 100 μl, and reacted at room temperature for 2 hours.

After washing with PBS-Tween, color was developed using a phosphatase substrate kit (KLP), the reaction was stopped with a 5 N sodium hydroxide aqueous solution, and the absorbance at 405 nm was measured by an automatic plate reader (Bio-Tek Instruments, Inc.).

The mean absorbance of two wells was calculated, and that showing an absorbance of not less than the mean absorbance +3 SD (standard deviation) of sera in group IV was judged as positive.

1-4) Result

In the smooth muscle contraction test using the guinea pig extracted trachea, death of animals on the way of the test was not found, and change in general condition ascribable to administration of the specimen was not recognized.

No difference was recognized in contractions induced by OVA, histamine and acetylcholine in the extracted trachea samples, between group I to which OVA and the remedy for allergies of the present invention were administered, and group II to which OVA sensitization was only effected. Also between group III to which OVA sensitization was not conducted and the remedy for allergies of the present invention was administered, and group IV to which no treatment was conducted, no difference was recognized in contractions induced by histamine and acetylcholine. In the group III and group IV, contraction induced by OVA was not recognized.

Figure 4:
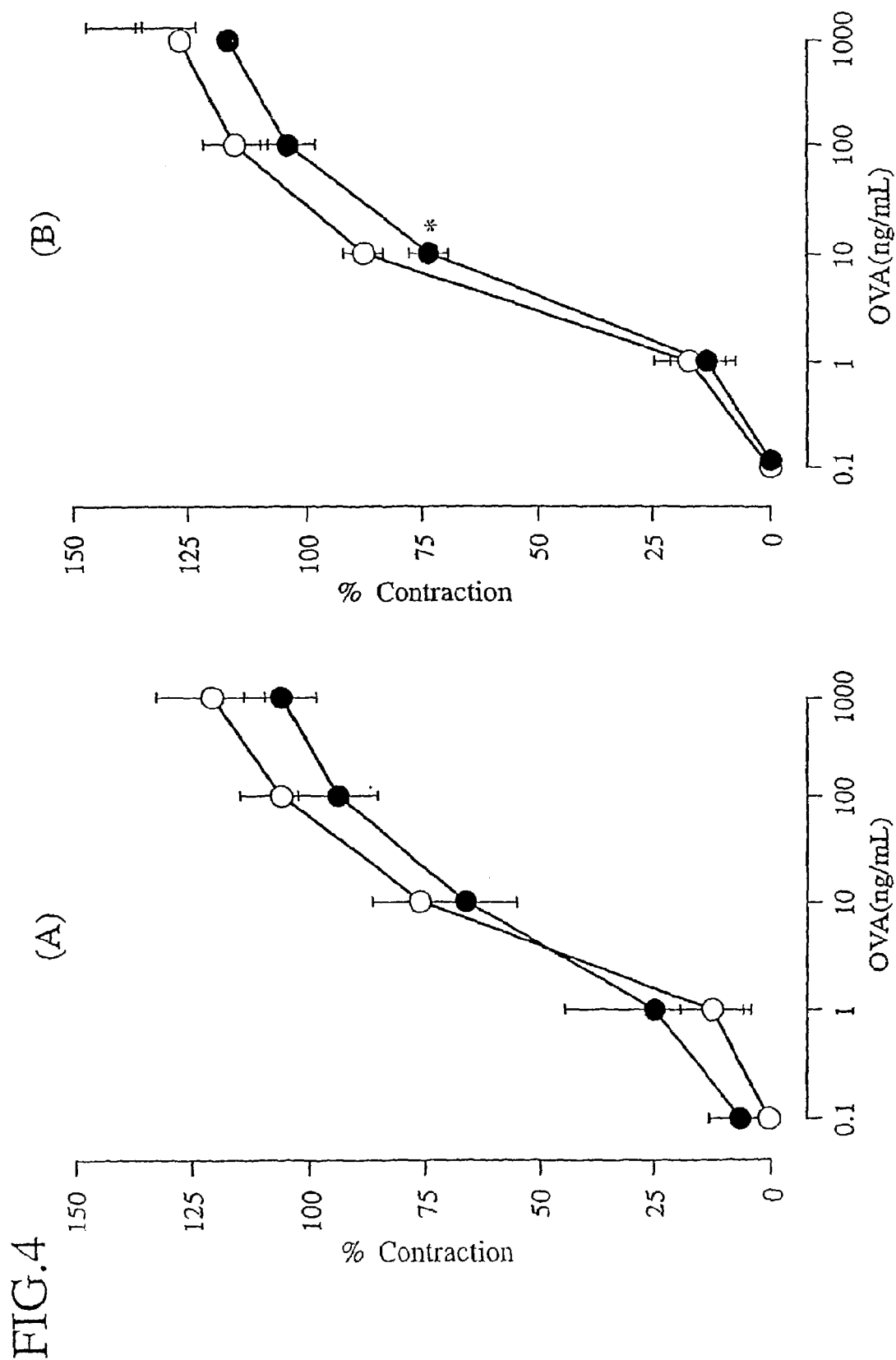
FIG. 4 is a graph showing the drug effect of a remedy for allergies of the present invention.

However, OVA-induced contraction in group II showed a suppression tendency by applying the remedy for allergies of the present invention to the organ bath (concentration in bath: 0.02%) (when OVA 10 ng/ml, $p<0.05$, see FIG. 4). Regarding histamine- and acetylcholine-induced contractions, the remedy for allergies of the present invention showed from no influence to suppression tendency in all groups (for example, in group m, when histamine $10^{-6}$ M, $p<0.05$).

Regarding the anti-OVA IgG antibody value in serum, the mean absorbance +3 SD (standard deviation) in group IV was 0.243. However, the mean absorbance of $10^4$-fold diluted sera in group I and group II conducted the sensitization-administration of OVA were 1.465 and 1.488, respectively, confirming the accomplishment of OVA sensitization. There was no significant difference in absorbance between group I and group II, and no influence was recognized due to administration of the remedy for allergies of the present invention.

2. Ear Swelling Test using Mouse

18 BALB/c male mice (BALB/c AnNCrj, SPF) of 6 weeks old were purchased, previously bred and quarantined for 1 week, 15 animals revealing no abnormality during the pre breeding period were used in the main test. The ear swelling test was conducted as described below.

The remedy for allergies of the present invention as a specimen was diluted with injection water to the given concentration. 1-chloro-2,4-dinitrobenzene (DNCB) used as an allergy inducing substance was dissolved in acetone:olive oil=4:1 mixture and used.

2-1) Sensitization Method

The following 3 groups were prepared.

TABLE 6

Constitution of Each Group

| | Administration substance and dose (administration volume) | | |
|---|---|---|---|
| Group | Sensitization (topical/subcutaneous, 0.1 mL) | Specimen (oral, 0.2 mL) | Number of animals |
| I | 0.1% DNCB/1% DNCB is mixed with the same volume of FCA | 2% fermentation product of the present invention | 5 |
| II | 0.1% DNCB/1% DNCB is mixed with the same volume of FCA | Injection water | 5 |
| III | acetone: olive oil mixed liquid (4:1)/olive oil | 2% fermentation product of the present invention | 5 |

0.1% DNCB dissolved in acetone: olive oil mixture or acetone: olive oil mixture was continuously applied for 4 days, and 12 days after, 1% DNCB dissolved in olive oil or olive oil was subcutaneously administered to the animals.

13 days after the final sensitization-administration, an ear swelling test was carried out. Administration of the remedy for allergies (fermentation product) of the present invention or injection water was conducted by oral administration for 3 days, from 3 days before the elicitation to a day before the elicitation.

2-2) Ear Swelling Test 13 days after the completion of sensitization-administration, 20 μL of 1% DNCB was applied on left ear and 20 μL of acetone:olive oil was applied on right ear of the animal, for elicitation. 24 hours after and 48 hours after the elicitation, thickness of left and right ears were measured each twice by Dial Thickness gauge (Sanpo Seisakusho). The mean values of two measurements were calculated to know a difference between the left ear thickness and the right ear thickness for each individual. Further, the average and standard deviation were calculated for each group, and a difference between groups was verified.

When a difference between two measured values is 0.1 mm or more, measurement was repeated again, and the closest two values were selected and averaged.

2-3) Result

In the ear swelling test using the BALB/c mice, death of animals on the way of the test was not observed, and change in the general condition of the animal ascribable to administration was not recognized.

In the measurement 24 hours after DNCB elicitation, in group I to which DNCB was sensitized and the remedy for allergies of the present invention was administered, an ear swelling reaction due to DNCB elicitation was significantly suppressed as compared with group II received DNCB elicitation alone ($p<0.05$, see FIG. 5). In reactions 48 hours after DNCB elicitation, no difference was recognized between group I and group II. In group III, control group, to which sensitization was carried out with acetone:olive oil and the remedy for allergies of the present invention was administered, swelling of auricle due to DNCB elicitation was scarcely recognized.

As described above, in the test using the extracted trachea of guinea pig, no influence of the orally administered remedy for allergies of the present invention was observed. On the other hand, when the remedy for allergies of the present invention was applied directly to the organ bath, a tendency of suppressing the contraction reaction was recognized for all stimuli by OVA, histamine and acetylcholine. From these results, it may possibly be deduced that the remedy for allergies of the present invention has a direct action on the plasma membrane to stabilize the membrane.

In the ear swelling test using BALB/c mice, in measurement 24 hours after DNCB elicitation, the reaction in the group administered the remedy for allergies of the present invention was significantly suppressed. Since the remedy for allergies of the present invention was administered for preceding 3 days to the of elicitation, the suppression recognized in the above test may be attributed not to the inhibition of the completion of sensitization but to the inhibition of signal transduction due to the elicitation from a sensitized lymphocyte to an inflammatory cell or to the suppression of an inflammatory reaction.

Thus, it may be deduced that the remedy for allergies of the present invention suppresses the liberation of inflammatory substances such as histamine through the stabilizing action on the plasma membrane and the like to show the anti-allergic action.

In the following, the examples of the practical treatment using the remedy for allergies of the present invention are described.

EXAMPLE 1

Remedy of Asthma

For a male child suffering from asthma of 7 years old, the remedy for allergies of the present invention was administered at morning and night, twice a day, each in an amount of about 30 to 50 mL After around one month administration, the symptom became lighter than before, and around about three months, the symptom became very well.

EXAMPLE 2

Remedy of Asthma

For a male of 65 years old suffering from coughing at morning and night due to asthma, the remedy for allergies of the present invention was administered at morning and night, twice a day, each in an amount of about 30 to 50 mL for about two weeks, then, coughing at morning and night disappeared.

EXAMPLE 3

Remedy of Atopic Dermatitis

For two adult females suffering from atopic dermatitis, the remedy for allergies of the present invention was administered at morning and night, twice a day, each in an amount of about 30 to 50 ml, then, after about two weeks administration, the symptom was improved in both females.

EXAMPLE 4

Remedy of Atopic Dermatitis

For a female of 21 years old suffering from atopic dermatitis from infancy and had inflammations at three regions, neck, joint of arm, and rear surface of knee, the remedy for allergies of the present invention was administered twice to three times a day, each in an amount of about 30 to 50 mL The inflammation on the rear surface of knee was remedied and original skin became visible, and 3 weeks after, the wound at neck disappeared, then, the inflammation at the left arm was remedied, and two months after, the inflammation at the right arm was also remedied, beautiful skin could be recovered.

Thus, from the results obtained by the administration to a lot of people, it was confirmed that the remedy for allergies of the present invention is effective in treating allergies. In the case of asthma or atopic dermatitis, the symptom became lighter from two weeks after the administration and about 3 months after, the symptom disappeared and the recurrence was not observed.

INDUSTRIAL APPLICABILITY

The remedy for allergies of the present invention can completely cure allergies, particularly, asthma and atopic dermatitis, by administration in a short period of time without causing side effects as compared with conventional allergic remedies. The present invention provides an extremely useful remedy for allergies.

What is claimed is:

1. An isolated yeast deposited under deposit number FERM BP-7499.

2. A fermentation product obtained by fermentation using the yeast according to claim 1, comprising a yeast identified as the yeast deposited under the deposit uumber FERM BP-7499.

3. The fermentation product according to claim 2, wherein the fermentation product is any of a remedy for allergic diseases, health food, or health drink.

4. The fermentation product of claim 2, comprising about $10^2$ to $10^5$/g of the yeast.

* * * * *